United States Patent [19]

Sierocuk et al.

[11] Patent Number: 5,697,913
[45] Date of Patent: Dec. 16, 1997

[54] TROCAR INCLUDING CANNULA WITH STEPPED REGION

[75] Inventors: Thomas J. Sierocuk, West Chester; Jorge N. Gutierrez; Charles S. Black, both of Cincinnati; Richard C. Smith, Loveland, all of Ohio

[73] Assignee: Ethicon Endo-Surgery, Inc., Cincinnati, Ohio

[21] Appl. No.: 694,980

[22] Filed: Aug. 9, 1996

[51] Int. Cl.⁶ ............................................. A61M 5/178
[52] U.S. Cl. ........................... 604/164; 604/174; 604/169
[58] Field of Search ................................... 604/164, 165, 604/167, 174, 175

[56] References Cited

U.S. PATENT DOCUMENTS

| | | | |
|---|---|---|---|
| 3,817,251 | 6/1974 | Hasson | 128/348 |
| 4,430,081 | 2/1984 | Timmermans | 604/167 |
| 4,655,752 | 4/1987 | Honkanen | 604/167 |
| 4,832,696 | 5/1989 | Luther | 604/164 |
| 5,002,557 | 3/1991 | Hasson | 604/174 |
| 5,147,316 | 9/1992 | Castillenti | 604/164 |
| 5,217,441 | 6/1993 | Shichman | 604/283 |
| 5,257,975 | 11/1993 | Foshee | 604/175 |
| 5,267,966 | 12/1993 | Paul | 604/167 |
| 5,271,380 | 12/1993 | Riek et al. | 128/4 |
| 5,330,497 | 7/1994 | Freitas et al. | 606/185 |
| 5,352,211 | 10/1994 | Merskelly | 604/180 |
| 5,403,336 | 4/1995 | Kieturakis et al. | 606/167 |
| 5,407,433 | 4/1995 | Loomas | 604/167 |
| 5,411,483 | 5/1995 | Loomas et al. | 604/167 |

Primary Examiner—Sam Rimell
Assistant Examiner—Luke J. Yeh
Attorney, Agent, or Firm—Matthew S. Goodwin

[57] ABSTRACT

A trocar including a cannula with a tubular sleeve having a stepped region thereon is disclosed. The stepped region has a plurality of discrete steps. Each step has a step floor and a step support base tapering radially inwardly from the step floor to an adjacent step floor. When the trocar is inserted through the body wall, and the stepped region of the sleeve of the cannula contacts the body wall, the force required to inadvertently pull the cannula out of the body wall when surgical instruments are withdrawn from the cannula increases. Thus, the tubular sleeve of the cannula increases the retention force of the cannula during surgery. The retention force is increased without appreciably affecting the force required to insert the trocar through the body wall. Additionally, these benefits are achieved without using helical threads or externally mounted stability devices, which add cost, complexity and increased risk of causing unwanted tissue trauma.

2 Claims, 4 Drawing Sheets

TROCAR INCLUDING CANNULA WITH STEPPED REGION

BACKGROUND OF THE INVENTION

This invention relates to a trocar cannula for providing tubular access to a surgical site within an internal bodily cavity for instruments which are used in endoscopic surgery. More specifically, it relates to a trocar including a cannula which has a tubular sleeve designed to enhance the retention of the sleeve within the body wall during surgery.

The desire to enhance the retention of a trocar cannula within a punctured body wall to prevent removal of the cannula when instruments are inserted into or withdrawn from the cannula during surgery has been well documented. Conventionally, integral threads have been mounted onto the sleeve of the cannula or, alternatively, external stability devices have been fitted over the sleeve to facilitate the fixation of the cannula within the body wall. For example, U.S. Pat. No. 5,271,380 describes the use of a helical thread mounted on the sleeve of the trocar cannula. U.S. Pat. No. 5,217,441 describes a device externally mounted to a trocar tube where the device has a sleeve with a helical thread. A locking trocar sleeve with an expandable mushroom hinge for expansion within the abdominal cavity to hold the sleeve in place is described in U.S. Pat. No. 5,330,497. Finally, an external stability pad for holding the sleeve of the trocar cannula in a fixed position is disclosed in U.S. Pat. No. 5,352,211.

Alternative retention devices for retaining a cannula during use in a fixed position are described in U.S. Pat. Nos. 3,817,251 and 5,257,975. A retention assembly for a skin seal which includes a helical thread formed on the outer surfaces of the sealing device is disclosed in U.S. Pat. No. 5,403,336.

Accordingly, it is becoming increasingly difficult to rely solely on the frictional interface between the punctured wall tissue and the sleeve of the trocar cannula to provide security and stability of the cannula during a surgical procedure when instruments are inserted and withdrawn from the cannula. This is true despite the development of trocars designed to cut a small entry incision into the body wall and thereafter expand or dilate the body wall tissue to accommodate the insertion and withdrawal of instruments. Although a greater frictional interference is provided when trocars designed to make smaller incisions are used, the retention force required to fix the sleeve of the cannula within the body wall during a surgical procedure may still exceed the force provided by the frictional interface. This is particularly true when a universal seal is mounted on the housing of the cannula to seal against surgical instruments over a wide range of diameters during surgery to maintain preperitoneum. Universal seals of the type which provide a seal against instruments having a diameter within a wide range of diameters are described, for example, in U.S. Pat. Nos. 5,407,433 and 5,411,483.

Unfortunately, the techniques described in the patents set forth above to enhance the fixation of the sleeve of the cannula within the body wall increases the forces required to insert the trocar into and through the incision. An increase in insertion force is highly undesirable because it makes more work for the surgeon, and decreases the amount of control the surgeon has during insertion. If the degree of control lessens, then the likelihood of inadvertent puncture of adjacent bodily tissue or organs is increased. In connection with the use of threaded devices mounted onto the sleeve of the cannula, the mounting of the device to the sleeve creates added steps for the surgeon which are a significant inconvenience. Additionally, the use of threads, particularly in combination with externally mounted devices, can be bulky. Therefore, the insertion of the trocar may be more traumatic, resulting in the tearing or bruising of adjacent tissue. Finally, externally mounted threads add additional components and cost to what are already costly surgical procedures.

Therefore, in view of the deficiencies which exist in the art, what is desired is a trocar which has a cannula sleeve adapted to retain its position within the body wall when instruments are inserted and withdrawn from the sleeve during surgery. Importantly, the retention of the sleeve needs to be established without additional componentry to add cost and complexity to the surgical procedure. Furthermore, the force to insert the trocar through the body wall should not significantly increase while the retention force of the sleeve within the body wall is appreciably enhanced. Finally, all of these benefits need to be achieved without increasing the trauma to tissue when the trocar is inserted through the body wall during the surgical procedure.

SUMMARY OF THE INVENTION

The invention is a trocar which comprises a trocar cannula. The trocar cannula includes a cannula housing and a tubular sleeve extending distally from the housing. The tubular sleeve has proximal and distal ends. The tubular sleeve has a stepped region on it between the proximal and distal ends. The stepped region has a plurality of discrete steps within the stepped region. Each of the discrete steps is defined by a circumferential step floor and a circumferential step support base descending distally from the step floor. The step support base tapers radially inwardly from the step floor to an adjacent step floor.

Significantly, the plurality of discrete steps within the stepped region of the tubular sleeve of the cannula increases the retention force of the cannula when the sleeve is positioned so that the stepped region is in contact with the body wall during the surgical procedure. Therefore, the pull-out force required to inadvertently remove the cannula from the body wall when a surgical instrument is withdrawn from the cannula is correspondingly increased. However, the increased retention force is not achieved by increasing the insertion force of the trocar. To the contrary, the force required to insert the trocar through the body wall into the internal body cavity at the surgical site is substantially unaffected even though the pull-out force is increased.

The unique design of each of the discrete steps within the stepped region of the sleeve of the cannula allows for increased retention force without substantially affecting the insertion force of the trocar. In particular, the tapering circumferential step support base provides structure to facilitate insertion of the trocar in a distal direction and inhibits unintended removal of the trocar sleeve in the proximal direction when instruments are withdrawn from the cannula.

In addition to enhancing the retention of the cannula sleeve within the body wall during surgery, this retention is achieved without the need for helical threads or externally mounted stability devices. Therefore, the surgeon does not need to take extra steps to insert the trocar, and trauma to the tissue during insertion or withdrawal of the trocar is minimized. Correspondingly, the costs of the surgical procedure are reduced.

The trocar of this invention can be used in any surgical procedure where it may facilitate the outcome of the procedure, including those procedures where trocars have conventionally been used.

DETAILED DESCRIPTION OF THE PREFERRED EMBODIMENT

Figure 1:
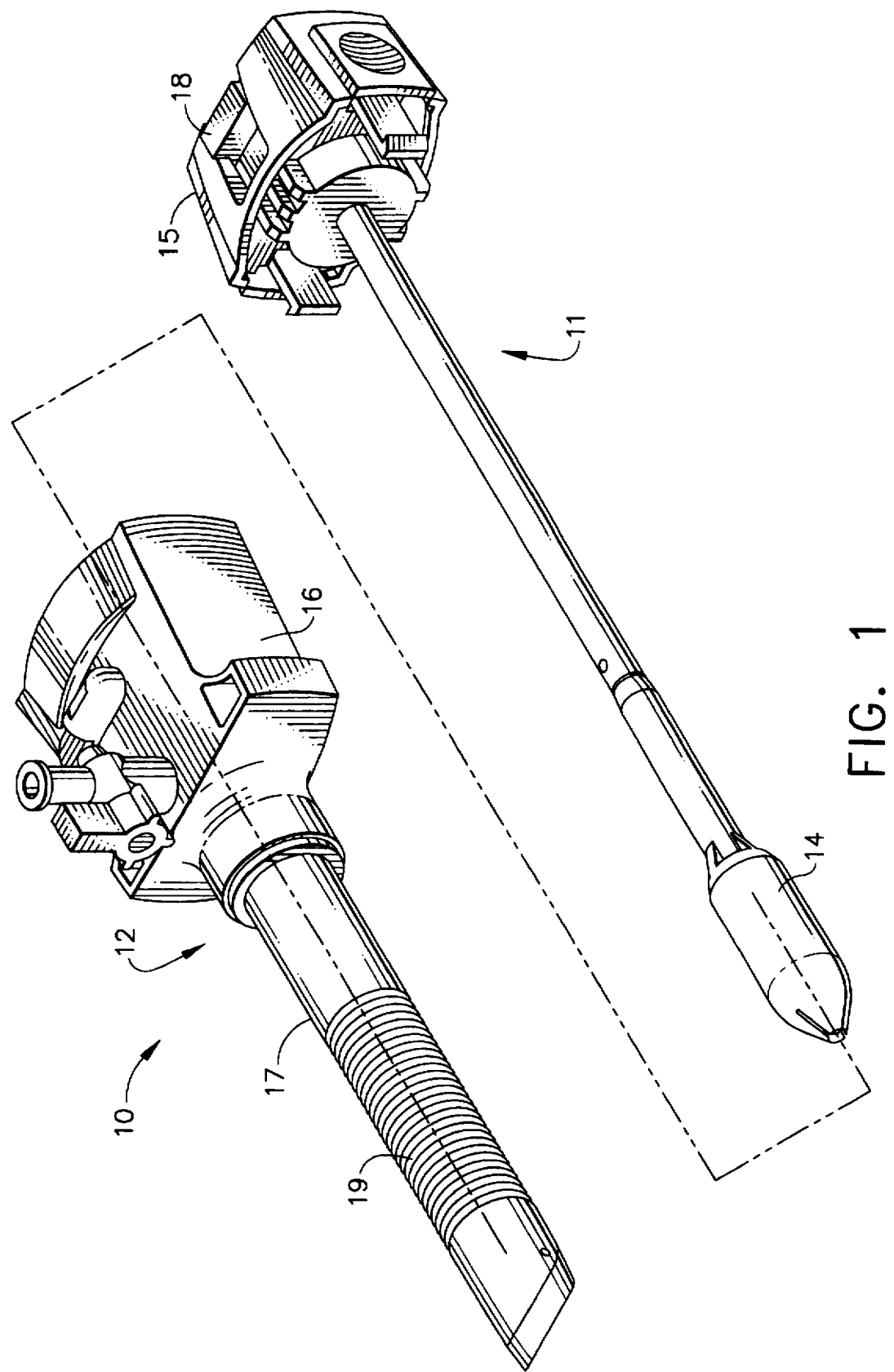
FIG. 1 is an exploded perspective view of a preferred trocar of this invention.
Figure 2:
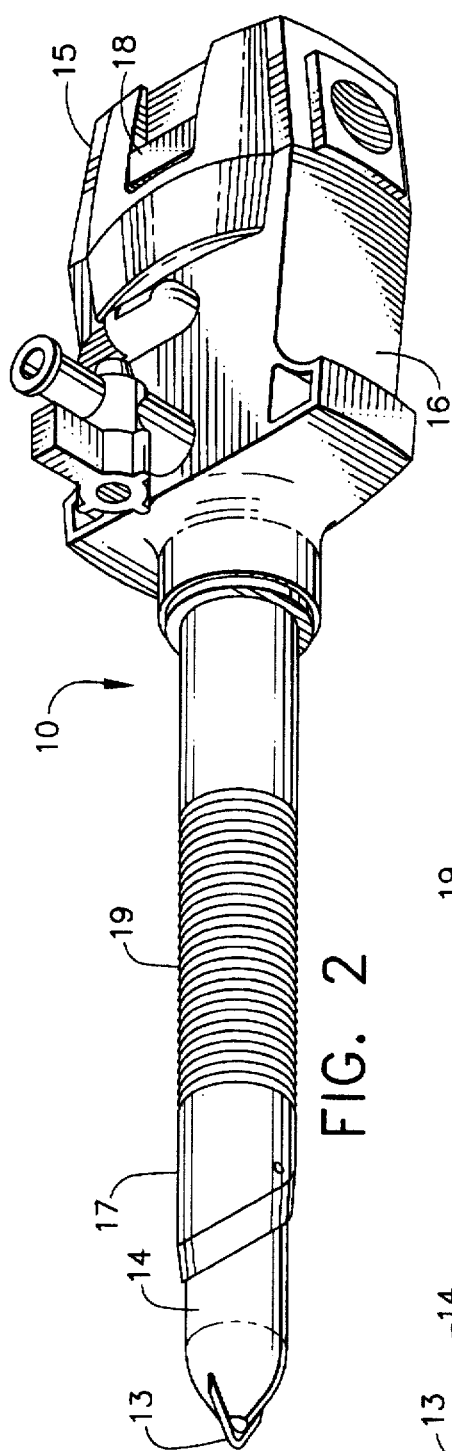
FIG. 2 is an assembled perspective view of the trocar of FIG. 1.
Figure 3:
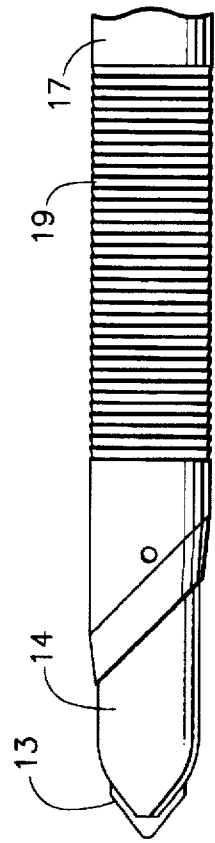
FIG. 3 is an enlarged fragmentary side elevational view of the distal end of the trocar of FIG. 2.

Referring initially to FIGS. 1–3, there is shown the preferred trocar 10 of this invention. The trocar has an obturator assembly 11 and a trocar cannula 12. The obturator assembly includes a flat, triangular-shaped blade 13 at a distal end thereof. A safety shield 14 covers the blade to prevent inadvertent puncture during use or handling. At the proximal end of the obturator assembly, there is an obturator housing 15. The safety shield of the obturator assembly is normally biased in an extended position as depicted in FIG. 1, and is movable within the obturator housing to a retracted position depicted in FIGS. 2 and 3 to expose the cutting blade.

The trocar cannula 12 of the trocar has a cannula housing 16 and a tubular sleeve 17 extending from the housing. The obturator assembly of the trocar is slidable into and through the trocar cannula. When fully inserted, the obturator housing is secured to the cannula housing, and the distal end of the obturator assembly, which includes the cutting blade enclosed within the safety shield, protrudes from the distal end of the trocar cannula.

In use, when the surgeon is ready to puncture the abdominal wall to provide access to an internal body cavity during surgery, he initially "arms" the trocar by sliding the arming button 18 on the obturator housing forwardly. This arming action releases the safety shield of the obturator assembly from a locked position where it is prevented from retracting to an unlocked position where retraction of the safety shield may occur. Once armed, the surgeon pushes the distal end of the obturator assembly of the trocar against the abdominal wall. As a result of the pressure exerted on the abdominal wall, the safety shield retracts, thus exposing the cutting blade of the obturator assembly. When the surgeon has fully punctured the abdominal wall, the safety shield returns to its normally extended position to enclose the cutting blade. Meanwhile, the trocar cannula has been moved forwardly concurrently with the obturator assembly of the trocar, so that it consequently has also been inserted through the abdominal wall to provide access to the internal body cavity. The surgeon can then remove the obturator assembly from the trocar cannula, and the surgeon can then use the trocar cannula as a tubular access for the insertion and withdrawal of endoscopic surgical instruments needed to accomplish the desired procedure.

In order to facilitate the retention of the trocar cannula 12 within the abdominal wall during the endoseopic procedure, a stepped region 19 is formed integrally on the tubular sleeve of the trocar cannula.

Figure 4:
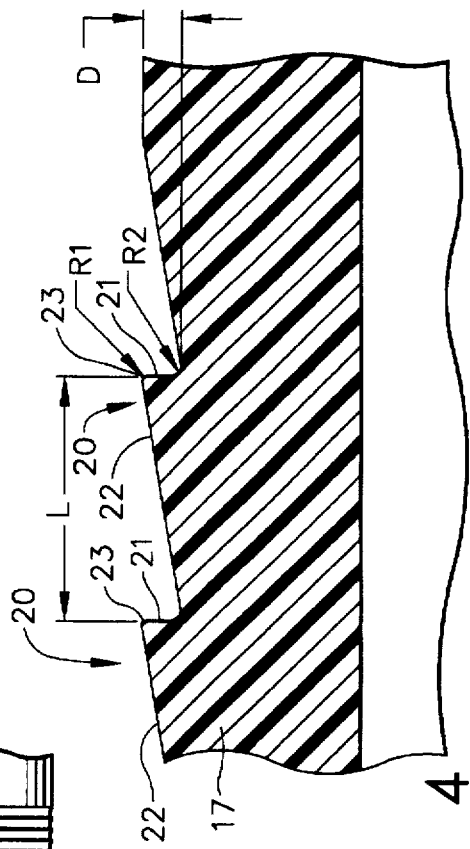
FIG. 4 is an enlarged fragmentary sectional view of the stepped region incorporated into the trocar cannula of FIG. 1.

Referring now particularly to FIG. 4, the reader will observe that the stepped region includes a plurality of discrete steps 20 embedded within the outer surface of the tubular sleeve 17 for providing the retention of the trocar cannula within the abdominal wall. Each of the discrete steps in the integral stepped region of the trocar cannula has a circumferential step floor 21 extending radially outwardly from the cannula sleeve, and a circumferential step support base 22 supporting the step floor. The support base has a length depicted as "L" in FIG. 4 and extends radially inwardly in the distal direction from the step floor to an adjacent step floor. The degree of taper of the step support base from the step floor to an adjacent step floor is defined in FIG. 4 as "D". In the most preferred embodiment, the radius "R1" depicted in FIG. 4, which defines the radius junction between the outer ledge 23 of the floor and the step support base, and radius "R2", which defines the radius junction between the step floor and the cannula sleeve, are such that the step floor is substantially perpendicular to the longitudinal axis of the cannula sleeve. Alternatively, the radii R1 and R2, as well as the dimensions D and L, can be varied to change the characteristics of the integral stepped region of the trocar cannula so that the degree of retention of the sleeve, or the pull-out force necessary to remove the sleeve, can be optimized.

Figure 5:
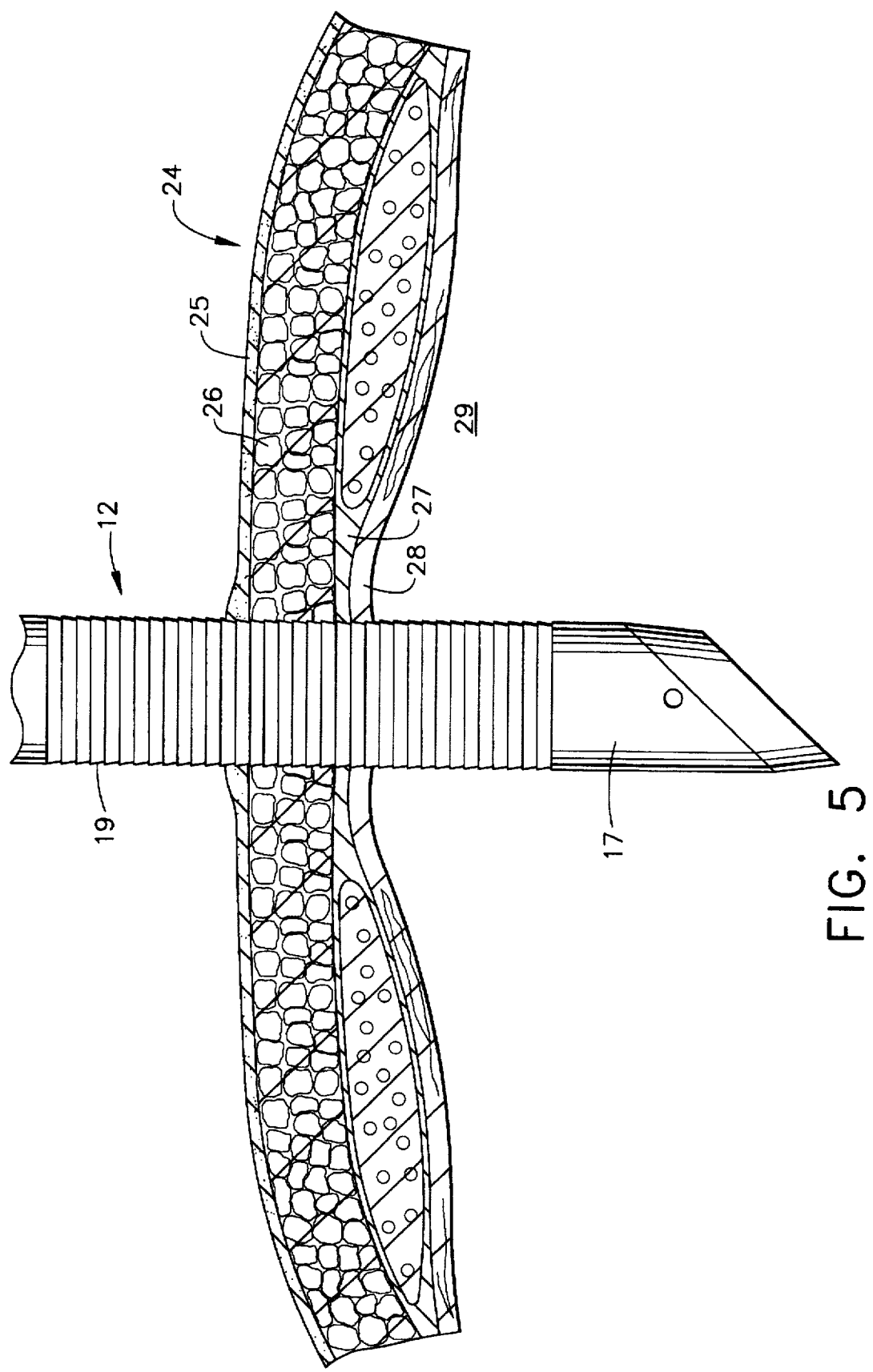
FIG. 5 is a fragmentary view showing the cannula of the trocar inserted through the various tissue layers of the abdominal wall, and the frictional contact between the stepped region of the cannula and the various tissue layers.
Figure 6:
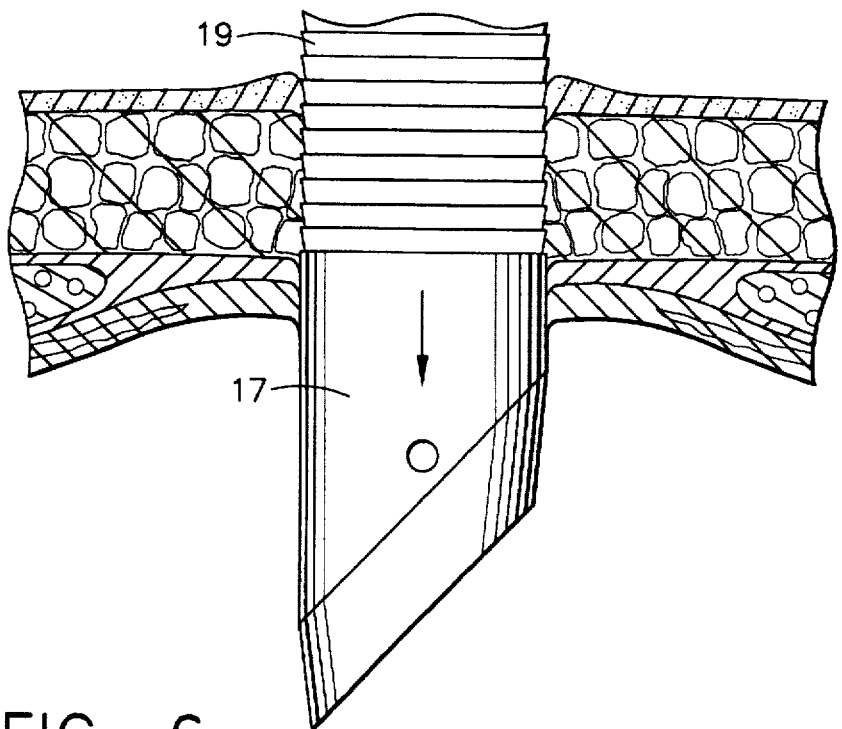
FIG. 6 is an enlarged fragmentary view similar to that of FIG. 5 illustrating the frictional forces exerted against the tissue when the trocar cannula is inserted into the abdominal cavity.
Figure 7:
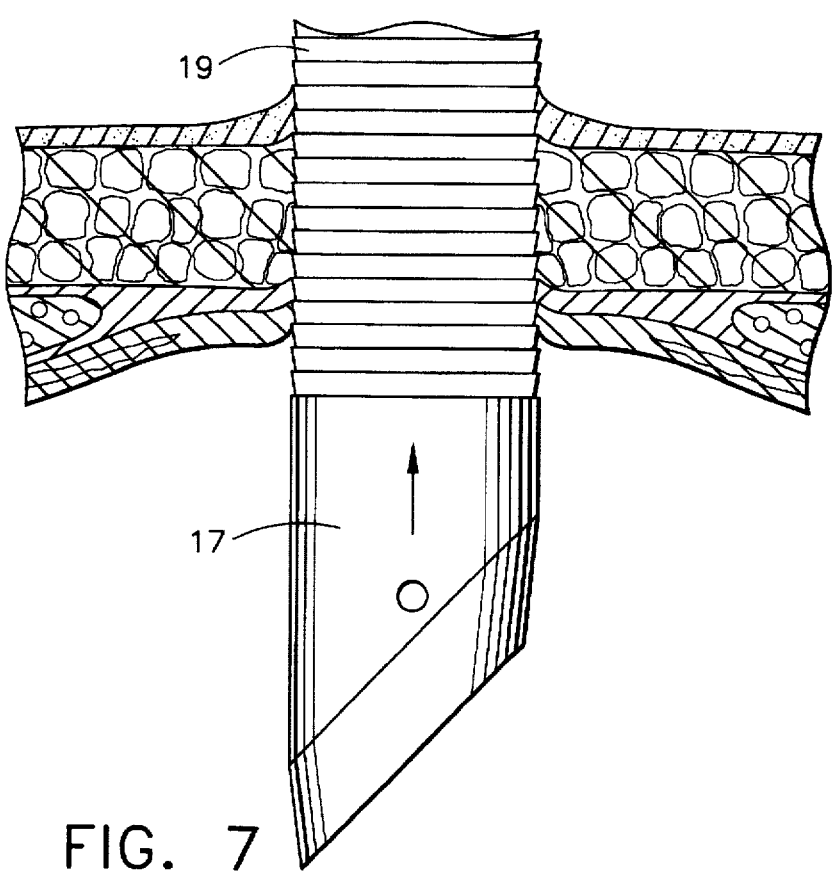
FIG. 7 is an enlarged fragmentary view similar to that of FIG. 5 illustrating the frictional forces exerted against the tissue when the trocar cannula is withdrawn from the abdominal cavity.

Referring now to FIGS. 5–7, when the cannula sleeve 17 of the trocar cannula 19 is inserted through the abdominal wall 24, it must necessarily pass through various layers of tissue. For example, when the cannula is inserted into and through the linea alba, it must pass through a skin layer 25, fat layer 26, fascia 27 and the peritoneum 28, before entering into the abdominal cavity 29. As depicted in FIG. 6, insertion force is minimized during insertion because the inward radial taper of each of the circumferential step support bases facilitates the gradual dilation of the tissue without generating a sudden, significant increase in frictional resistance as the cannula is pushed downwardly into and through the tissue layers in the direction depicted by the directional arrow. In contrast, as depicted in FIG. 7, high pull-out forces are retained because the circumferential step floors provide significant frictional resistance to upward movement of the cannula sleeve during removal of the trocar cannula in the direction of the directional arrow. Thus, the trocar of this invention enables the surgeon to minimize the insertion force necessary to enter the abdominal cavity without unnecessarily increasing significantly the force required to remove the cannula sleeve of the trocar from the abdominal cavity following the surgical procedure.

Although this invention has been described in connection with its most preferred embodiment, those skilled in this art will envision readily apparent modifications and alterations of the preferred embodiment which fall well within the scope and spirit of the claimed invention. Consequently, the reader should not take this detailed description of the preferred embodiment as any indication that the claims which define the invention and appear below should be narrowly construed in any way.

What is claimed is:

1. A trocar comprising a trocar cannula, said trocar cannula including a cannula housing and a tubular sleeve having a longitudinal axis extending distally from said housing, said tubular sleeve having proximal and distal ends and an outer surface, wherein said outer surface of said tubular sleeve has a stepped region embedded within said outer surface between said proximal and distal ends, said stepped region being spaced from said cannula housing and positioned to frictionally contact a tissue layer when said trocar is inserted through the tissue layers said stepped region having a plurality of discrete steps, and each of said discrete steps is defined by a circumferential step floor extending substantially perpendicularly from the longitudinal axis and a circumferential step support base descending distally, from said step floor, said step support base tapering radially inwardly from said step floor to an adjacent step floor.

2. The trocar of claim 1 wherein said stepped region is integral with said outer surface of said cannula sleeve.

* * * * *